(12) United States Patent
Kerschbaumer et al.

(10) Patent No.: US 8,399,249 B2
(45) Date of Patent: Mar. 19, 2013

(54) PROCEDURE FOR THE GENERATION OF A HIGH PRODUCER CELL LINE FOR THE EXPRESSION OF A RECOMBINANT ANTI-CD34 ANTIBODY

(75) Inventors: Randolf Kerschbaumer, Klosterneuberg (AT); Petra Boeck-Taferner, Stixneusiedl (AT); Friedrich Scheiflinger, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/389,265

(22) Filed: Feb. 19, 2009

(65) Prior Publication Data

US 2009/0221003 A1 Sep. 3, 2009

Related U.S. Application Data

(60) Provisional application No. 61/066,682, filed on Feb. 21, 2008.

(51) Int. Cl.
*C12N 5/06* (2006.01)
*C12N 63/00* (2006.01)
(52) U.S. Cl. ........................................ 435/326; 435/455
(58) Field of Classification Search ........................ None
See application file for complete search history.

(56) References Cited

U.S. PATENT DOCUMENTS

| 2006/0183201 | A1 | 8/2006 | Nair | |
|---|---|---|---|---|
| 2007/0196422 | A1* | 8/2007 | Kutryk et al. | 424/423 |
| 2009/0215645 | A1* | 8/2009 | Rong et al. | 506/10 |

FOREIGN PATENT DOCUMENTS

| EP | 0 695 346 B1 | 2/1996 |
|---|---|---|
| EP | 0 765 478 B1 | 4/1997 |
| EP | 1 083 226 B1 | 3/2001 |

OTHER PUBLICATIONS

Gryn, J., et al., "Rapid Communication: Factors Affecting Purification of CD34+ Peripheral Blood Stem Cells Using the Baxter Isolex 300i," *Journal of Hematotherapy & Stem Cell Research*, vol. 11(4), pp. 719-730 (2002).
Hu, S-z, et al., "Minibody: A Novel Engineered Anti-Carcinoembryonic Antigen Antibody Fragment (Single-Chain Fv-$C_H3$) Which Exhibits Rapid, High-Level Targeting of Xenografts," *Cancer Research*, Vo. 56, pp. 3055-3061 (Jul. 1, 1996).
Kawabata, Y., et al., "Clinical Applications of CD34+ Cell-selected Peripheral Blood Stem Cells," *Therapeutic Apheresis and Dialysis*, vol. 7(3), pp. 298-304 (2003).
Krause, D., et al., "CD34: Structure, Biology, and Clinical Utility," *Blood*, vol. 87(1), pp. 1-13, (Jan. 1, 1996).
Sanchez, P., et al., "Structure of a third murine immunoglobulin λ light chain variable region that is expressed in laboratory mice," *Proc. Natl. Acad. Sci. USA*, vol. 84, pp. 9185-9188 (Dec. 1987).
Tseng-Law, J., et al., "Identification of a peptide directed against the anti-CD34 antibody, 9C5, by phage display and its use in hematopoietic stem cell selection," *Experimental Hematology*, vol. 27(5), pp. 936-945 (1999).
Vaughan, T., et al., "Human Antibodies with Sub-nanomolar Affinities Isolated from a Large Non-immunized Phase Display Library," *Nature Biotechnology*, vol. 14(3), pp. 309-314 (Mar. 1996).
Watts, M., et al., "Variable product purity and functional capacity after CD34 selection: a direct comparison of the CliniMACS® (v21) and Isolex® 300i (v2:5) clinical scale devices," *British Journal of Haematology*, vol. 118(1), pp. 117-123 (2002).
Zhu, Z., et al., "Remodeling domain interfaces to enhance heterodimer formation," *Protein Science*, vol. 6, pp. 781-788 (1997).
Glamann, Joakim et al.; "Characterization of a Macaque Recombinant Monoclonal Antibody That Binds to a CD4-Induced Epitope and Neutralizes Simian Immunodeficiency Virus"; 2000, *Journal of Virology*, vol. 74, No. 15, pp. 7158-7163.
Jostock, Thomas; "Emerging Alternative Production Systems"; 2007, *Handbook of Therapeutic Antibodies*, pp. 445-466.
Lansdorp, P.M. et al.; "CD34 Epitopes"; 1989, *Leucocyte Typing IV*, pp. 826-827.
Lansdorp, P.M. et al.; "Selective Expression of CD45 Isoforms on Functional Subpopulations of CD34+ Hemopoietic Cells from Human Bone Marrow"; 1990, *J. Exp Med.*, vol. 172, pp. 363-366.
Qian, Weizhu et al.; "Development of new versions of anti-human CD34 monoclonal antibodies with potentially reduced immunogenicity"; 2008, *Biochemical and Biophysical Research Communications*, vol. 367, pp. 497-502.
Schmitt, C. et al.; "Expression of CD34 on human B cell precursors"; 1991, *Clin. Exp. Immunol.*, vol. 85, pp. 168-173.
Wurm, Florian M.; "Production of recombinant protein therapeutics in cultivated mammalian cells"; 2004, *Nature Biotechnology*, vol. 22, No. 11, pp. 1393-1398.
"Monoclonal Antibodies Detecting Human Antigens CD34 (My10)"; 2002, *Announcement Becton Dickinson Biosciences*, pp. -13.

* cited by examiner

*Primary Examiner* — Michail Belyavskyi
(74) *Attorney, Agent, or Firm* — Kilpatrick Townsend & Stockton LLP

(57) ABSTRACT

The present invention relates to cell capture assay for the selection of a high producer cell line expressing anti-CD34 antibodies that recognize the CD34 membrane-protein in the cell membrane. The monoclonal antibody secreted by the hybridoma cell line 9C5/9069 binds to human CD34 and is used to isolate stem cells. The DNA sequences encoding for the antibody heavy and light chain have been identified, isolated from the hybridoma cells and cloned into appropriate expression vectors. After co-transfection of the heavy and light chain genes into HEK293T or in CHO cells either conditioned medium or purified antibody were assessed for binding to CD34 protein located in the cell membrane in different cell capture assays. The binding of the antibody to CD34-positive cells could be shown with these assays for several cell lines.

6 Claims, 11 Drawing Sheets

SEQUENCE LISTING

<160> NUMBER OF SEQ ID NOS: 8

<210> SEQ ID NO 1
<211> LENGTH: 1341
<212> TYPE: DNA
<213> ORGANISM: Artificial Sequence
<220> FEATURE:
<223> OTHER INFORMATION: Description of Artificial Sequence:synthetic
      anti-CD34 antibody heavy chain

<400> SEQUENCE: 1

```
gaggttcagc tgcagcagtc tggacctgag ctggtgaagc ctggggcttc agtgaagata      60
tcctgcaagg cttctggtta ttcatttatt ggctacttta tgaactgggt gatgcagagc     120
catggaagga gccttgagtg gattggacgt attaatcctt acaatggtta tactttctac     180
aaccagaagt tcaagggcaa ggccacattg actgtagaca atcctctag cacagcccac     240 atggagctcc ggagcctggc atctgaggac tctgcagtct attattgtgc aagacacttt     300
aggtacgacg gggtttttta ctatgctatg gactactggg gtcaaggaac ctcagtcacc     360
gtctcctcag ccaaaacgac accccatct gtctatccac tggcccctgg atctgctgcc     420
caaactaact ccatggtgac cctgggatgc ctggtcaagg gctatttccc tgagccagtg     480
acagtgacct ggaactctgg atccctgtcc agcggtgtgc acaccttccc agctgtcctg     540
```

```
cagtctgacc tctacactct gagcagctca gtgactgtcc cctccagcac ctggcccagc    600
gagaccgtca cctgcaacgt tgcccacccg gccagcagca ccaaggtgga caagaaaatt    660
gtgcccaggg attgtggttg taagccttgc atatgtacag tcccagaagt atcatctgtc    720
ttcatcttcc ccccaaagcc caaggatgtg ctcaccatta ctctgactcc taaggtcacg    780
tgtgttgtgg tagacatcag caaggatgat cccgaggtcc agttcagctg gtttgtagat    840
gatgtggagg tgcacacagc tcagacgcaa ccccgggagg agcagttcaa cagcactttc    900
cgctcagtca gtgaacttcc catcatgcac caggactggc tcaatggcaa ggagttcaaa    960
tgcagggtca acagtgcagc tttccctgcc cccatcgaga aaaccatctc caaaaccaaa   1020
ggcagaccga aggctccaca ggtgtacacc attccacctc ccaaggagca gatggccaag   1080
gataaagtca gtctgacctg catgataaca gacttcttcc ctgaagacat tactgtggag   1140
tggcagtgga tgggcagcc agcggagaac tacaagaaca ctcagcccat catggacaca   1200
gatggctctt acttcgtcta cagcaagctc aatgtgcaga gagcaactg ggaggcagga    1260 aatactttca cctgctctgt gttacatgag ggcctgcaca accaccatac tgagaagagc   1320
ctctcccact ctcctggtaa a                                             1341
```

<210> SEQ ID NO 2
<211> LENGTH: 447
<212> TYPE: PRT
<213> ORGANISM: Artificial Sequence
<220> FEATURE:
<223> OTHER INFORMATION: Description of Artificial Sequence:synthetic anti-CD34 antibody heavy chain

<400> SEQUENCE: 2

```
Glu Val Gln Leu Gln Gln Ser Gly Pro Glu Leu Val Lys Pro Gly Ala
  1               5                  10                  15

Ser Val Lys Ile Ser Cys Lys Ala Ser Gly Tyr Ser Phe Ile Gly Tyr
             20                  25                  30

Phe Met Asn Trp Val Met Gln Ser His Gly Arg Ser Leu Glu Trp Ile
         35                  40                  45

Gly Arg Ile Asn Pro Tyr Asn Gly Tyr Thr Phe Tyr Asn Gln Lys Phe
     50                  55                  60

Lys Gly Lys Ala Thr Leu Thr Val Asp Lys Ser Ser Thr Ala His
 65                  70                  75                  80

Met Glu Leu Arg Ser Leu Ala Ser Glu Asp Ser Ala Val Tyr Tyr Cys
                 85                  90                  95

Ala Arg His Phe Arg Tyr Asp Gly Val Phe Tyr Ala Met Asp Tyr
            100                 105                 110

Trp Gly Gln Gly Thr Ser Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
```

```
                210                 215                 220
Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
                260                 265                 270

Val Gln Phe Ser Trp Phe Val Asp Asp Val Glu Val His Thr Ala Gln
                275                 280                 285

Thr Gln Pro Arg Glu Glu Gln Phe Asn Ser Thr Phe Arg Ser Val Ser
                290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
                340                 345                 350

Pro Pro Lys Glu Gln Met Ala Lys Asp Lys Val Ser Leu Thr Cys Met
                355                 360                 365

Ile Thr Asp Phe Phe Pro Glu Asp Ile Thr Val Glu Trp Gln Trp Asn
370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
                420                 425                 430

His Asn His His Thr Glu Lys Ser Leu Ser His Ser Pro Gly Lys
                435                 440                 445

<210> SEQ ID NO 3
<211> LENGTH: 660
<212> TYPE: DNA
<213> ORGANISM: Artificial Sequence
<220> FEATURE:
<223> OTHER INFORMATION: Description of Artificial Sequence:synthetic
      anti-CD34 antibody light chain

<400> SEQUENCE: 3
caacttgtgc tcactcagtc atcttcagcc tctttctccc tgggagcctc agcaaaactc      60
acgtgcacct tgagtagtca gcacagtacg ttcaccattg aatggtatca gcaacagcca     120
ctcaagcctc ctaagtatgt gatggatctt aagaaagatg gaagccacag cacaggtgat     180
ggggttcctg atcgcttctc tggatccagc tctggtgctg atcgctacct tagcatttcc     240
aacatccagc ctgaagatga agcaacatac atctgtggtg tgggtgatac aattaaggaa     300
caatttgtgt atgttttcgg cggtggaacc aaggtcactg tcctaggtca gcccaagtcc     360
actcccactc tcaccgtgtt tccaccttcc tctgaggagc tcaaggaaaa caaagccaca     420
ctggtgtgtc tgatttccaa cttttccccg agtggtgtga cagtggcctg aaggcaaat      480 ggtacaccta tcacccaggg tgtggacact tcaaatccca ccaagagggg caacaagttc     540
atggccagca gcttcctaca tttgacatcg gaccagtgga gatctcacaa cagttttacc     600
tgtcaagtta cacatgaagg ggacactgtg gagaagagtc tgtctcctgc agaatgtctc     660

<210> SEQ ID NO 4
<211> LENGTH: 220
```

```
<212> TYPE: PRT
<213> ORGANISM: Artificial Sequence
<220> FEATURE:
<223> OTHER INFORMATION: Description of Artificial Sequence:synthetic
      anti-CD34 antibody light chain

<400> SEQUENCE: 4
```

Gln Leu Val Leu Thr Gln Ser Ser Ala Ser Phe Ser Leu Gly Ala
 1               5                  10                  15

Ser Ala Lys Leu Thr Cys Thr Leu Ser Ser Gln His Ser Thr Phe Thr
             20                  25                  30

Ile Glu Trp Tyr Gln Gln Pro Leu Lys Pro Pro Lys Tyr Val Met
         35                  40                  45

Asp Leu Lys Lys Asp Gly Ser His Ser Thr Gly Asp Gly Val Pro Asp
     50                  55                  60

Arg Phe Ser Gly Ser Ser Ser Gly Ala Asp Arg Tyr Leu Ser Ile Ser
 65                  70                  75                  80

Asn Ile Gln Pro Glu Asp Glu Ala Thr Tyr Ile Cys Gly Val Gly Asp
                 85                  90                  95

Thr Ile Lys Glu Gln Phe Val Tyr Val Phe Gly Gly Gly Thr Lys Val
            100                 105                 110

Thr Val Leu Gly Gln Pro Lys Ser Thr Pro Thr Leu Thr Val Phe Pro
        115                 120                 125

Pro Ser Ser Glu Glu Leu Lys Glu Asn Lys Ala Thr Leu Val Cys Leu
    130                 135                 140

Ile Ser Asn Phe Ser Pro Ser Gly Val Thr Val Ala Trp Lys Ala Asn
145                 150                 155                 160

Gly Thr Pro Ile Thr Gln Gly Val Asp Thr Ser Asn Pro Thr Lys Glu
                165                 170                 175

Gly Asn Lys Phe Met Ala Ser Ser Phe Leu His Leu Thr Ser Asp Gln
            180                 185                 190

Trp Arg Ser His Asn Ser Phe Thr Cys Gln Val Thr His Glu Gly Asp
        195                 200                 205

Thr Val Glu Lys Ser Leu Ser Pro Ala Glu Cys Leu
    210                 215                 220

```
<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:synthetic
      PCR 5' primer heavy chain

<400> SEQUENCE: 5
acttggcgcg cactctgagg ttcagctgca g                               31

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence:synthetic
      PCR 3' primer heavy chain

<400> SEQUENCE: 6
catctagagc ggccgcatca tttaccagga gagtgggaga g                    41

<210> SEQ ID NO 7
<211> LENGTH: 47
<212> TYPE: DNA
```

-continued

```
<213> ORGANISM: Artificial Sequence
<220> FEATURE:
<223> OTHER INFORMATION: Description of Artificial Sequence:synthetic
      PCR 5' primer light chain

<400> SEQUENCE: 7
gagtcattct gcgcgcacag tcaacttgtg ctcactcagt catcttc                47

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence:synthetic
      PCR 3' primer light chain

<400> SEQUENCE: 8
gagtcattct gcggccgctc attagagaca ttctgcagga gacagactc              49
```

PROCEDURE FOR THE GENERATION OF A HIGH PRODUCER CELL LINE FOR THE EXPRESSION OF A RECOMBINANT ANTI-CD34 ANTIBODY

CROSS-REFERENCE TO RELATED APPLICATIONS

This application claims benefit of U.S. provisional application No. 61/066,682, filed Feb. 21, 2008, which application is herein incorporated by reference.

FIELD OF THE INVENTION

The present invention relates to a procedure for the generation of recombinant antibodies that recognize the CD34 membrane-protein in it's natural environment, the cell membrane and cell cultures expressing high yields of said antibodies.

BACKGROUND OF THE INVENTION

Antibodies specific for antigens that are integrated into the cell membrane (e.g. receptors) are a valuable tool in research and clinical application. The application of many standard procedures for high-throughput screening of such antibodies is hampered by the fact that the protein has to be used apart from its natural environment, the plasma membrane. Usually, the soluble portion of membrane proteins are expressed recombinantly and applied in screening assays. It is therefore more desirable to screen for antibodies that interact with the antigen that is integrated in the membrane.

Fluorescence-activated cell-sorting (FACS) is a specialized type of flow cytometry and provides a method for sorting cells or analyzing the functional interaction of cells with a variety of molecules including antibodies. FACS methods or other currently used technologies (e.g. immunofluorescence microscopy) are time consuming and thus not optimal for a high-throughput screening during a cell selection process. These methods are usually applied at the end of the selection process to verify the quality of e.g. an antibody. During the selection process of cell lines expressing recombinant antibodies the cells are routinely screened only for their productivity by measuring the amount of expressed antibodies. In the worst case this could finally lead to a cell line expressing high amounts of antibodies which may not have the expected functionality, i.e. that the antibodies do not bind to the respective antigen (membrane-protein) in it's natural environment, the cell membrane This may be especially the case if the antibody to be recombinantly expressed is not well characterized prior to expression. It would be therefore advantageous to screen not only for high expression during the selection process but also for the binding of the required antibody to the membrane-protein in the cell membrane.

One typical example for this problem is the murine antibody secreted by the mouse hybridoma cell line 9C5/9069. It binds to the human cluster designation 34 (CD34) antigen and can be used for the isolation of CD34 positive stem cells. The 9C5/9069 mouse hybridoma was originally developed by Lansdorp et al. (Leucocyte Typing IV, 1989; 826-7, Oxford University Press, Oxford). There is an established production process for said antibody using the hybridoma cell line. However, the current process faces some limitations regarding the upscale of production and improvement of production yield. In addition the antibody is not characterized in detail, i.e. the sequence is not known.

In deciding for a production cell line expressing anti-CD34 antibody, one parameter is an acceptable cell-specific average productivity (determined e.g. as picogram antibody produced per cell per day, pcd) and sufficient yield in the cell culture, measured e.g. as mg/L of antibody. These parameters are usually determined by standard ELISA methods.

The anti-CD34 antibodies are routinely used for the selection of stem cells and there are clinical applications of said selected stem cells for a variety of diseases (Kawabata et al. Ther Apher Dial. 2003; 7:298-304).

EP1083226A1 discloses devices containing antibodies recognizing CD4 or CD34 and their use for the separation of CD4 or CD34 positive cells.

EP0765478B1 teaches to select CD34 target cells by reacting specific anti-CD34 antibody to surface antigen and then disrupting the complex formed with peptide displacer.

EP0695346A1 discloses the separation of hematopoietic progenitor cells on the basis of binding to a specific cell surface antigen such as CD34.

Interaction of ligands (e.g. antibodies) with cell surface proteins are often detected by growing adherent cells in wells, fixation of the cells and incubating them with the respective labeled ligand. These methods usually suffer from the fact that fixation results in (partial) denaturation of the cell surface proteins and thus might lead to falsified results.

However, none of these disclosures teaches a high-throughput assay for the selection of anti-CD34 antibodies that recognize the CD34 membrane-protein in it's natural environment, the cell membrane.

Therefore it was the inventive task of the present invention to develop a novel assay allowing to test the binding of antibodies to proteins in it's natural environment in a high-throughput format, preferably on microplates.

SUMMARY OF THE INVENTION

A cell capture assay was developed to assess the binding of recombinant antibodies to antigens in it's natural environment, e.g. a cell membrane. The usefulness of the assay was shown by the development of a cell line expressing higher amounts of antibodies as the corresponding 9C5/9069 hybridoma cell line. The monoclonal antibody secreted by the cell line 9C5/9069 binds to human CD34 and is used to isolate stem cells. The sequence of the antibody light and heavy chain have been determined by N-terminal sequencing of the light and heavy chain at the protein level and by isolating and sequencing the respective genes at the DNA level. The genes encoding for the heavy and the light chain were cloned into two separate expression vectors allowing co-expression of both genes. The cell capture assay was first used to examine the binding of anti-CD34 antibodies in transiently transfected HEK293T cells. Then a recombinant cell line for the stable production of the anti-CD34 antibody was generated. After the transfection of the two vectors into the dihydrofolate reductase (DHFR)-deficient CHO cell line DXB11 the cell capture assay showed to be useful for the selection of high producer cell lines expressing anti-CD34 antibodies binding to CD34 in the cell membrane not only during amplification of the cell lines, but also during the adaptation of selected cell clones to grow in medium free from serum and animal derived components. Dose response and competition cell capture assays have proven to be a valuable tool for in depth characterization of the antibody.

DETAILED DESCRIPTION OF THE INVENTION

Figure 1:
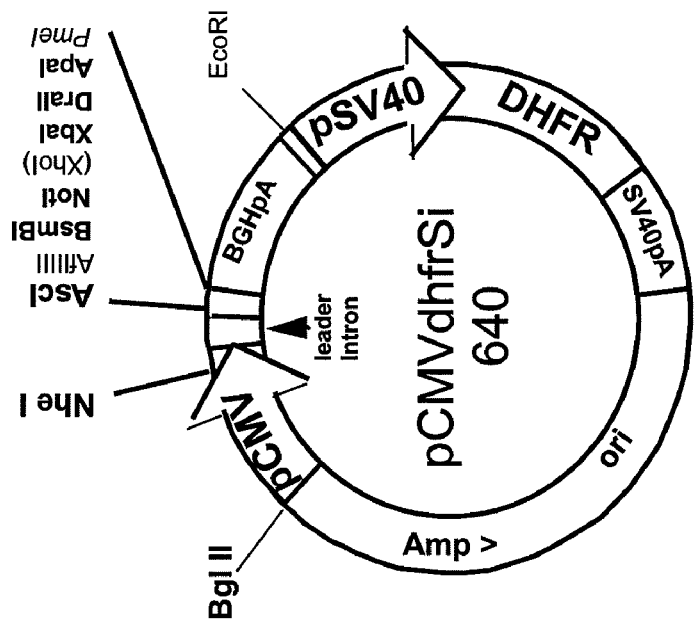
FIG. 1 shows a schematic diagram of vectors pCMVneoSi 639 and pCMVdhfrSi 640.
Figure 1:
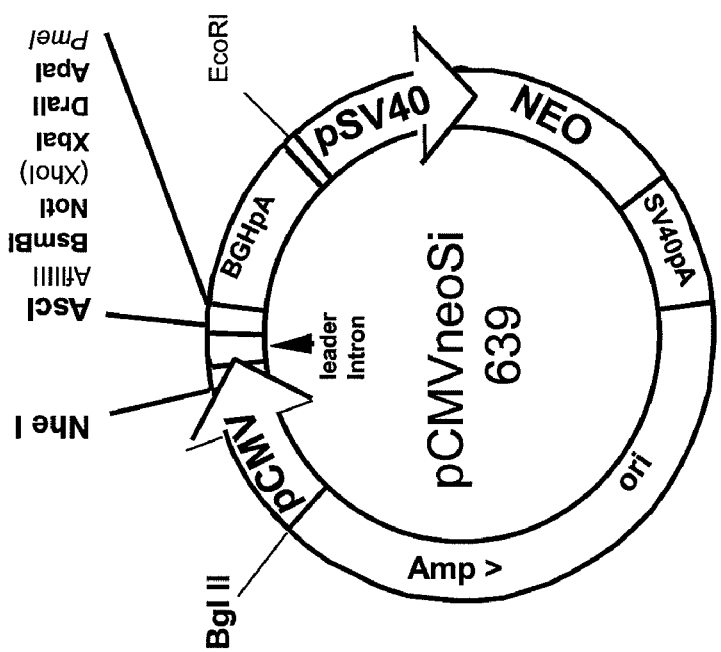

The present invention relates to a procedure for the generation of recombinant anti-CD34 antibodies that recognize the CD34 membrane-protein in it's natural environment, the cell membrane and cell cultures expressing high yields of said antibodies.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The human cluster designation 34 (CD34) antigen (Krause et al. Blood 1996; 87:1-13) refers to a heavily glycosylated type I transmembrane protein mainly expressed on early lymphohematopoietic stem and progenitor cells, small-vessel endothelial cells, embryonic fibroblasts, and some cells in fetal and adult nervous tissue.

There are clinical applications of CD34+ cell-selected stem cells for a variety of diseases (Kawabata et al. Ther Apher Dial. 2003; 7:298-304). For example peripheral blood stem cells are increasingly used for stem cell transplantation after high dose chemotherapy, autologous transplantation studies, and in tumor cell purging. There is also the potential for CD34+ stem cells to treat a severe form of coronary artery disease called chronic myocardial ischemia. Potential exists for angiogenesis (creation of new blood vessels) and possible myogenesis (creation of new cardiac tissue) to help treat cardiovascular diseases in patients who are described as having no other viable options for treating their disease and the symptoms of severe angina.

As used herein, "antibody" is meant to refer generally to an immunoglobulin molecule that is immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability e.g., Fab', F(ab')$_2$, Fab, Fv and rIgG (see, e.g., Kuby, Immunology, 3$^{rd}$ Ed., W.H. Freeman & Co., New York 1998). The term also encompasses recombinant single chain Fv fragments (scFv). The term further includes bivalent or bispecific molecules, diabodies, triabodies, and tetrabodies. Bivalent and bispecific molecules are described in, e.g., Zhu et al. (Protein Sci. 1997; 6:781-9, and Hu et al. (Cancer Res. 1996; 56:3055-61).

An antibody immunologically reactive with a particular antigen can be generated by recombinant methods such as selection of libraries of recombinant antibodies in phage or similar vectors, see, e.g., Vaughan et al. (Nature Biotech. 1996; 14:309-14), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs".

The anti-CD34 antibody according to the present invention may be derived from any vertebrate, e.g. a mammal. In one specific example of the present invention, the anti-CD34 antibody is murine anti-CD34 antibody.

According to the present invention, the term "anti-CD34 antibody" does not underlie a specific restriction and may include any anti-CD34 antibody, obtained via recombinant DNA technology, or a biologically active derivative thereof. In a preferred embodiment of the present invention the amino acid and nucleotide sequences of the light and heavy chains are as disclosed in SEQ-ID NOs 1-4.

The terms "isolated" or "purified" refer to an antibody that is substantially or essentially free from components that normally accompany it. Purity and homogeneity are typically determined using analytical chemistry techniques such as polyacrylamide gel electrophoresis or high performance liquid chromatography. A protein or nucleic acid that is the predominant species present in a preparation is substantially purified.

The production of anti-CD34 antibody according to the present invention may include any method for the generation of recombinant DNA by genetic engineering, e.g. via reverse transcription of RNA and/or amplification of DNA and cloning into expression vectors.

Recombinant antibodies can be produced by means of conventional expression vectors, such as bacterial vectors (e.g., pBR322 and its derivatives), pSKF or eukaryotic vectors (e.g., such as pMSG, SV40, and pCMV vectors). Those sequences that encode the antibody can be provided with regulatory sequences that regulate the replication, expression and/or secretion from the host cell. These regulatory sequences comprise, for instance, promoters (e.g., CMV or SV40) and signal sequences. The expression vectors can also comprise selection and amplification markers, such as the dihydrofolate reductase gene (DHFR), hygromycin-B-phosphotransferase, and thymidine-kinase. The components of the vectors used, such as selection markers, replicons, enhancers, can either be commercially obtained or prepared by means of conventional methods. The vectors can be constructed for the expression in various cell cultures, e.g., in mammalian cells such as CHO, COS, fibroblasts, insect cells, yeast or bacteria such as E. coli. In some instances, cells are used that allow for optimal glycosylation of the expressed protein.

In a preferred embodiment of the present invention the heavy and light chains of the antibody were cloned in two separate pCMV expression vectors with the two different selection markers neomycin and DHFR allowing co-transfection and co-expression of both genes in the same cell line.

The production of anti-CD34 antibody may include any method known in the art for the introduction of recombinant DNA into eukaryotic cells by transfection, e.g. via electroporation or microinjection. For example, the recombinant expression of anti-CD34 antibody can be achieved by introducing an expression plasmid containing the anti-CD34 antibody encoding DNA sequence under the control of one or more regulating sequences such as a strong promoter, into a suitable host cell line by an appropriate transfection method resulting in cells having the introduced sequences stably integrated into the genome. The lipofection method is an example of a transfection method which may be used according to the present invention.

The production of anti-CD34 antibody may also include any method known in the art for the cultivation of said transformed cells, e.g. in a continuous or batch-wise manner, and the expression of the anti-CD34 antibody, e.g. constitutive or upon induction. For example the nucleic acid coding for anti-CD34 antibody contained in the host organism of the present invention is expressed via an expression mode selected from the group consisting of induced, transient, and permanent expression.

The host cell type according to the present invention may be any eukaryotic cell. In a preferred embodiment the cell is a mammalian cell with the ability to perform posttranslational modifications of anti-CD34 antibody. For example said mammalian cell is derived from a mammalian cell line, like for example a cell line selected from the group consisting of SkHep-, CHO—, HEK293-, and BHK-cells. In specific examples of the present invention, the anti-CD34 antibody is expressed transiently in HEK293T cells and stably in the DHFR-deficient CHO cell line DXB11 and adding G418 as second selection marker.

There is no particular limitation to the media, reagents and conditions used for culturing the cells in the cell culture of the present invention including culturing the cells in a continuous or batch-wise manner. The cells may be cultured also under serum-free or serum- and protein-free conditions. In a specific example of the present invention the cells are cultured in ProCHO4, a chemically defined medium containing low concentrations of recombinant insulin, and Excell325 PF, a protein-free medium containing soy hydrolysate.

Additionally, the production of the anti-CD34 antibody may include any method known in the art for the purification of the anti-CD34 antibody, e.g. via anion exchange chromatography or affinity chromatography. In one preferred embodiment the anti-CD34 antibody can be purified from cell culture supernatants by protein A or Protein G sepharose columns. The purified anti-CD34 antibody may be analyzed by methods known in the art for analyzing recombinant proteins, e.g. standard ELISA techniques and by electrophoresis techniques including immuno-blotting.

Another aspect of the invention relates to an assay for measuring the binding of the expressed antibodies in a cell capture assay. A variety of methods for a cell capture assay may be possible. In one preferred embodiment of the present invention the cell capture assay is a dose response cell capture assay and in another preferred embodiment a competitive cell capture assay.

Anti-CD34 antibodies of the present invention can be utilized to quantify and purify CD34 positive lymphohematopoietic stem/progenitor cells for research and for clinical uses.

The anti-CD34 antibody of the present invention can be also used for example in systems selecting progenitor cells. The Baxter Isolex 300i system is one specific example of said systems. Examples for reproducible CD34+ cell purification with the Baxter Isolex 300i over a wide range of starting conditions are described in Gryn et al. (J Hematother Stem Cell Res. 2002; 11:719-30) and Watts et al. (Br J. Haematol. 2002; 118:117-23).

In the Baxter Isolex 300i CD34+ cell purification system an anti-CD34 antibody is mixed with cells to permit binding to CD34+ cells. Dynabeads® M-450 coated with sheep anti-Mouse IgG (Invitrogen/Gibco, Lofer, Austria) recognizing the murine-derived anti-CD34. A magnetic field is used to separate the CD34+ cell-bead complexes from the rest of the cell suspension. The unbound antibody is removed by washing steps. PR34+ Stem Cell Releasing Agent is used to separate antibodies/beads from CD34+ cells. The separated CD34+ cells are then washed to remove residual reagents, such as mouse and sheep antibodies, and finally collected.

The anti-CD34 antibody of the present invention may be also used in a pharmaceutically acceptable composition comprising an auxiliary agent, e.g. selected from the group consisting of a pharmaceutically acceptable carrier, diluent, salt, buffer, or excipient. The pharmaceutical composition of the invention may be a solution or a lyophilized product.

As used herein, the term "pharmaceutically acceptable" means approved by a regulatory agency of US or EU government or listed in the U.S. Pharmacopeia or other generally recognized pharmacopeia for use in animals, and more particularly in humans.

The present invention will be further illustrated in the following examples, without any limitation thereto.

EXAMPLES

Example 1

Sequence Determination and Cloning of the Anti-CD34 Antibody Light and Heavy Chain Supernatants of 9C5/9069 hybridoma cells expressing anti-CD34 antibody were harvested by centrifugation, sterile filtered (Nalge Nunc, Graz, Austria) and purified by affinity chromatography on a protein G sepharose column (Amersham Biosciences, Vienna, Austria). The antibody was eluted from the column by a glycine buffer (Merck, Vienna, Austria) pH 2.8. Fractions containing the purified antibody were pooled, and dialyzed against PBS pH 7.2-7.4. The N-terminal amino acids of the heavy and light chains of the purified antibody were sequenced according to standard protocols.

Total RNA was isolated from hybridoma cells using the TRIzol Reagent (Sigma-Aldrich, Vienna, Austria) according to standard protocols. The RNA was used for synthesis of cDNA applying the Ready-To-Go™-you-Prime First-Strand Beads Kit (Amersham Biosciences) according to the manufacturer's instructions. The cDNA was then used as a template for amplification of the light chain gene and heavy chain gene in separate PCR reactions using primers:

SEQ-ID NO 5: 5' primer heavy chain
5'-ACTTGGCGCG CACTCTGAGGTT CAGCTGCAG-3'

SEQ-ID NO 6: 3' primer heavy chain
5'-CATCTAGAGC GGCCGCATCA TTTACCAGGA GAGTGGGAGA G-3'

SEQ-ID NO 7: 5' primer light chain
5'-GAGTCATTCT GCGCGCACAG TCAACTTGTG CTCACTCAGT CATCTTC-3'

SEQ-ID NO 8: 3' primer light chain
5'-GAGTCATTCT GCGGCCGCTC ATTAGAGACA TTCTGCAGGA GACAGACTC-3'

Purified PCR fragments were sequenced according to standard protocols. The sequence of the N-terminal 15 amino acids of the anti-CD34 antibody heavy chain and the sequence of the first 20 amino acids of the light chain corresponded to the respective DNA sequences (SEQ-ID NOs 1 and 2, 3 and 4, respectively).

Comparison of the antibody sequences with the Kabat-database (Kabat et al. Sequences of Proteins of Immunological Interest, 5th edition, U.S. Department of Health and Human Services, National Institute of Health, Bethesda, Md., 1991) showed that the anti-CD34 antibody is a murine IgG1 with a lambda light chain that has a rare V lambda gene segment (Sanchez et al. Proc Natl Acad Sci USA. 1987; 84:9185-8).

Figure 2:
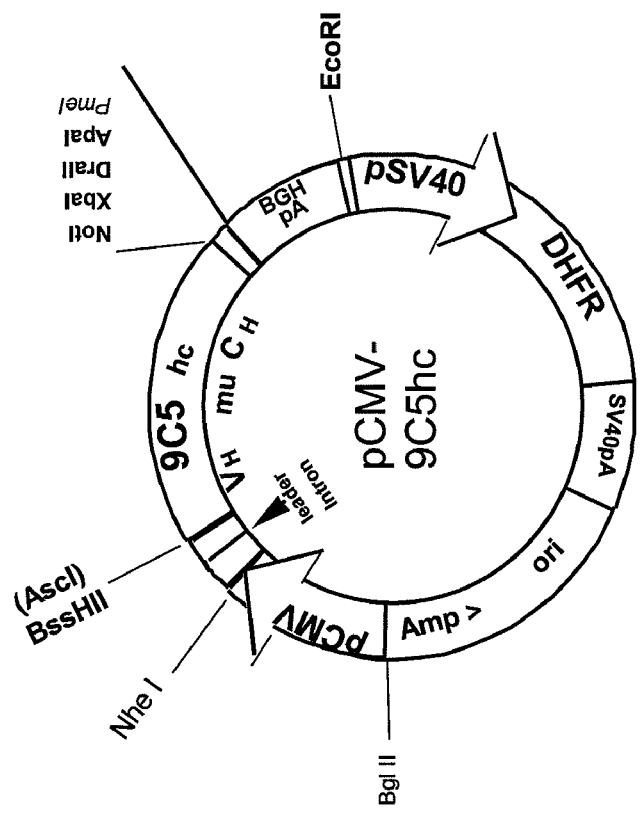
FIG. 2 shows a schematic diagram of plasmids pCMV-9C5lc and pCMV-9C5hc expressing the light and heavy chain of anti-CD34 9C5 antibody.
Figure 2:
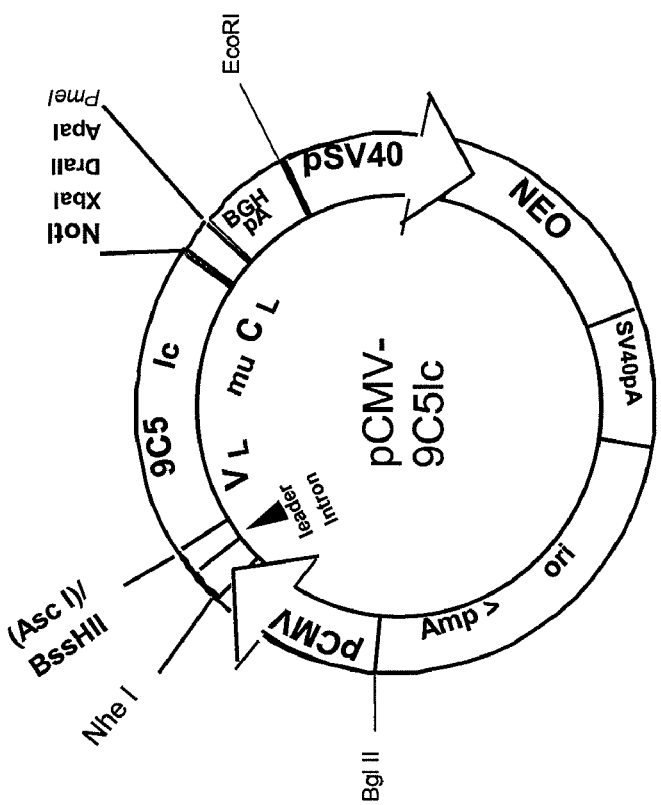

The light chain gene was cloned into the AscI and NotI sites of modified pCMV vector pCMVneoSi 639 and the heavy chain gene was cloned into the SfiI, NotI sites of modified pCMV vector pCMVneoSi 640 to obtain pCMV-9C5lc and pCMV-9C5hc, respectively (FIGS. 1 and 2). After standard cloning procedures the vectors were purified using commercially available kits (Qiagen, Vienna, Austria).

Example 2

Figure 3:
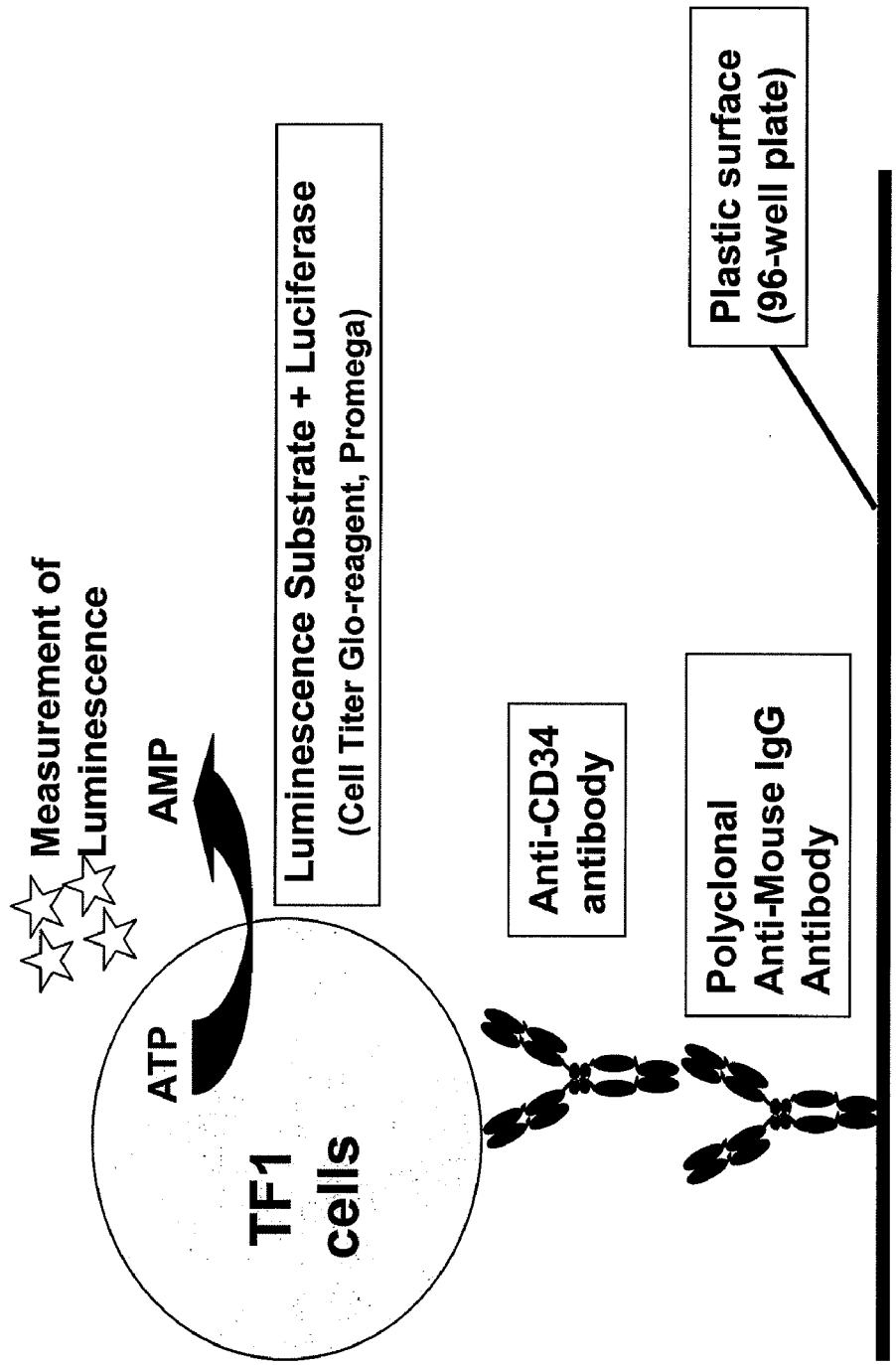
FIG. 3 shows a schematic diagram of the cell capture assay.

Development of the Cell Capture Assay 96-well microplates (Maxisorp, Nalge Nunc) were coated with polyclonal anti-mouse IgG antibody developed in goats (Jackson Immuno Research, Suffolk, UK) or in sheep (Baxter Oncology, Halle, Germany). After washing with PBS, either conditioned medium containing the anti-CD34 antibody was added and incubated overnight at 4° C. or purified antibody was diluted in DMEM medium (Invitrogen/Gibco, Lofer, Austria) supplemented with 10% FCS (PAA Laboratories, Pasching, Austria) and 1% penicillin/streptomycin (Invitrogen/Gibco) prior to incubation. Subsequently, plates were washed with PBS and TF-1 cells (ATCC CRL-2003) were added at a cell density of $1\times10^5$ cells/mL. TF-1 cells were cultivated in RPMI medium (Invitrogen/Gibco). The bound anti-CD34 antibody captures the TF-1 cells by binding to the CD34 present on the surface of the cells. After washing steps to remove the unbound cells, the Cell Titer-Glo reagent from the CellTiter-Glo Luminescent Cell Viability Assay Kit (Promega, Mannheim, Germany) was added. This reagent gives a luminescence signal proportional to the number of viable cells based on an ATP-dependent luciferase reaction (FIG. 3).

Example 3

Cell Capture Assay for Testing Anti-CD34 Antibodies Transiently Expressed in HEK293T Cells HEK293T cells (GenHunter, Nashville, USA) were propagated in DMEM medium (Invitrogen/Gibco), supplemented with 0.1% Gentamycin, 1% MEM non-essential amino acids, 1% antibiotic/antimycotic and 10% FBS (all Invitrogen/Gibco).

Transient transfection with pCMV-9C5lc and pCMV-9C5hc was carried out using GeneJuice (Merck/Novagen) according to the instructions of the manufacturer with four different light chain vector preparations in combination with one heavy chain vector preparation. As negative controls, the heavy chain vector and the light chain vector were transfected separately. Transfected cells were incubated up to three weeks after transfection. The conditioned medium was harvested after 3 days of incubation and replaced by fresh medium.

Figure 4:
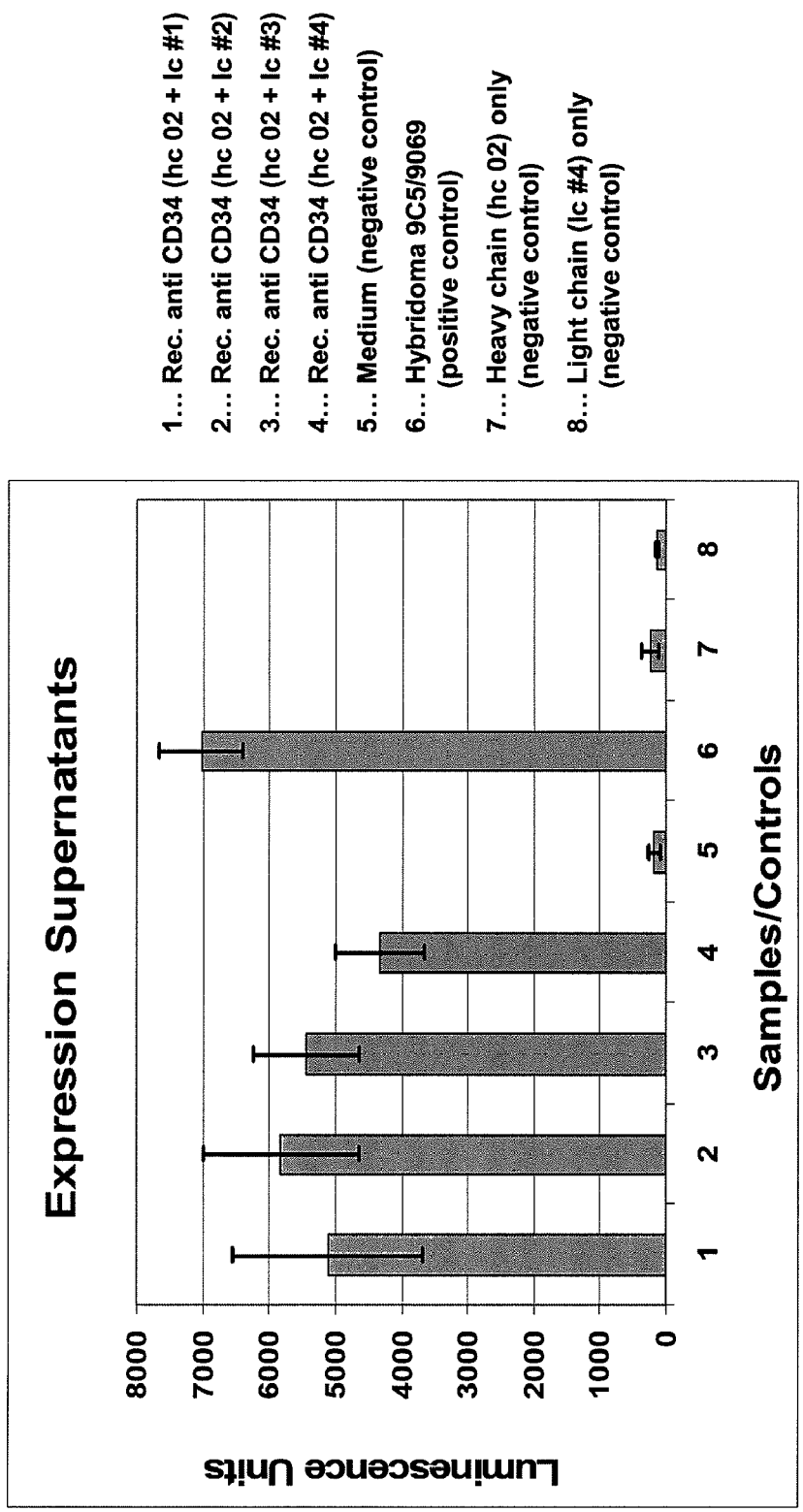
FIG. 4 shows the cell capture assay for anti-CD34 antibody in conditioned supernatant of transiently transfected HEK293T cells.

The expression of mouse IgG was first verified by the Easy Titer Mouse IgG Assay (Pierce) according to the manufacturer's instructions. To test the functionality of the antibodies the supernatants were tested in the cell capture assay. The results obtained are depicted in FIG. 4 (hc 02, heavy chain vector; lc #1, lc #2, lc #3, and lc #4, respective light chain vector preparations, hybridoma supernatant=positive control) and indicate that the transiently expressed recombinant anti-CD34 antibody is capable of capturing the CD34-positive TF-1 cells. The mean of two independent experiments is depicted.

The conditioned media of the control transfections (light chain vector or heavy chain vector alone, lanes 7 and 8, respectively) did not give a signal, nor did unconditioned medium (lane 5). Thus it could be concluded that the combination of the heavy and light chain genes isolated from the hybridoma cell line 9C5/9069 leads to the expression of a functional anti-CD34 antibody. From this result it can be expected that after a stable transfection and a selection process for a high producer clone the finally expressed anti-CD34 antibody would also retain its binding to the CD34 membrane-protein.

Furthermore, in a large scale expression experiment 23 triple flasks (Nunclon Surface, Nalge Nunc) and one cell factory (Nalge Nunc) were co-transfected and incubated for three weeks. Supernatant was harvested twice a week and replaced by fresh medium resulting in 18 L of supernatant. Finally 7.9 mg of anti-CD34 antibody were obtained. A dilution series of the purified antibody was tested in the cell capture assay and compared with the hybridoma-derived antibody. The results depicted in FIG. 5 (n=4, control antibody n=2) show that the antibody gave a dose response similar to the hybridoma-derived anti-CD34 antibody, giving further evidence for the binding of the antibody to the CD34 membrane-protein.

Example 4

Figure 6:
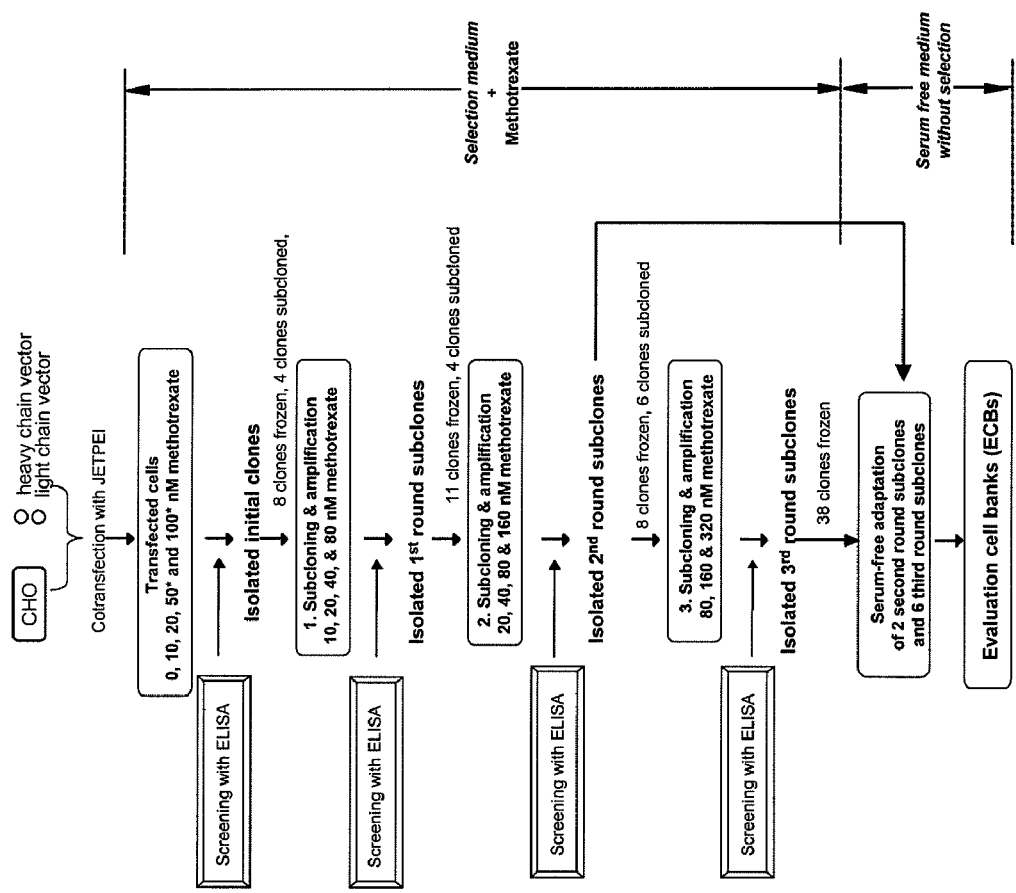
FIG. 6 shows a flow diagram for the generation of stable CHO cell lines expressing anti-CD34 antibody.
Figure 7:
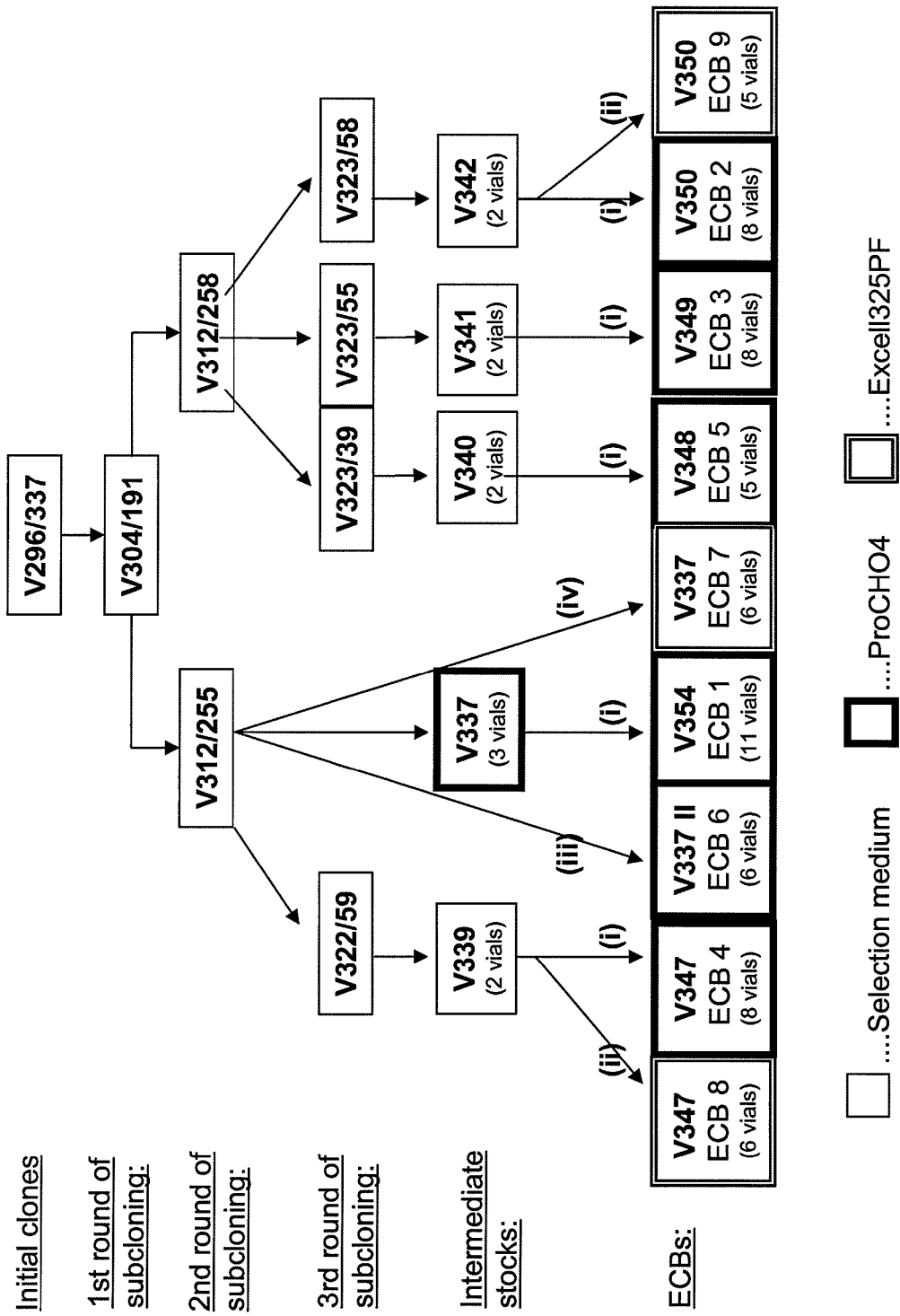
FIG. 7 shows the pedigree of evaluation cell banks of CHO cell lines expressing anti-CD34 antibody.

Generation of Stable CHO Cell Lines Producing High Amounts of Anti-CD34 Antibodies CHO-DXB11 were stably transfected with 1.5 µg plasmid DNA of the light and heavy chain, respectively (pCMV-9C5lc and pCMV-9C5hc). After three days in full medium cells were seeded into selection medium supplemented with methotrexate as indicated in FIG. 6. The selection medium was free of hypoxanthin, glycine and thymidine and was supplemented with G418 and therefore allowed a double selection. Cells were tested for their productivity by measuring the antibody concentration after 24 hours of incubation in serum-free selection medium by a standard ELISA method and by counting the cells.

Figure 5:
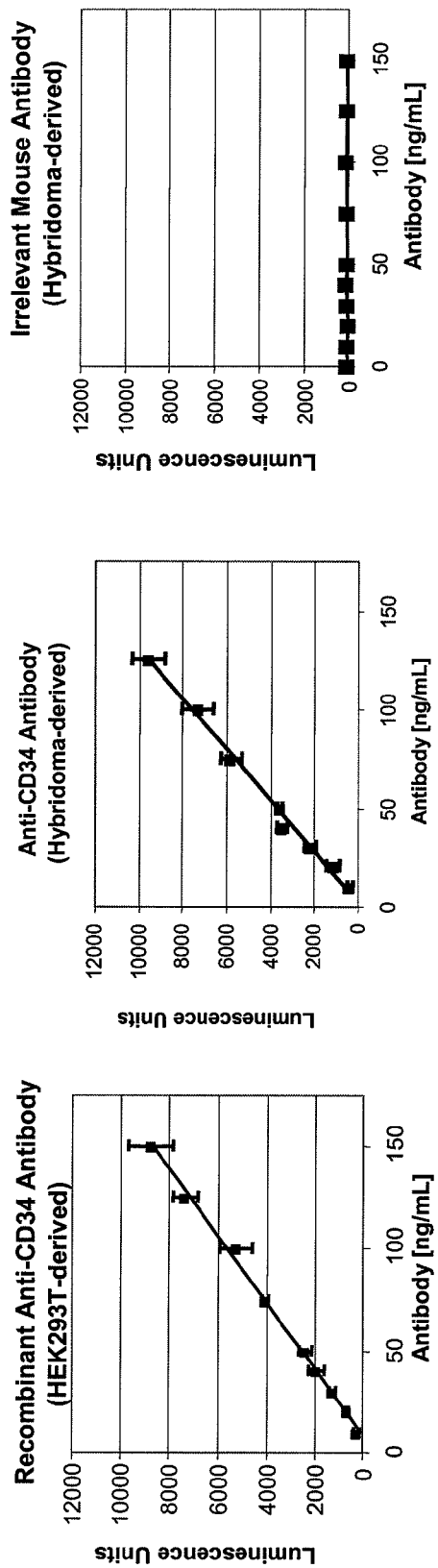
FIG. 5 shows the cell capture assay of purified recombinant anti—CD34 antibody from transiently transfected HEK293T cells.

Three rounds of subcloning and amplification as schematically shown in FIG. 6 were carried out. Then seven different media were tested to adapt cell clones for growth in medium free from serum and animal derived components: BAV-SP (Baxter), BAV-CD (Baxter), ProCHO4 (Cambrex, North Brunswick, USA), ProCHO-AT (Cambrex), Excell325 PF (distributed by Sigma-Aldrich), Excell-CD CHO, (distributed by Sigma-Aldrich) and CD-CHO (Invitrogen/Gibco). Only adaptation to ProCHO4, a chemically defined medium containing low concentrations of recombinant insulin, and Excell325 PF, a protein-free medium containing soy hydrolysate, was successful. The pedigree of the successfully adapted cell lines that were frozen as evaluation cell banks (ECBs) is depicted in FIG. 5. The pcd was calculated for each day. The pcd values are equivalent to $\mu g/(10^6 \text{ cells} \times 24 \text{ hours})$ and were calculated according to the formula: pcd at day $x$=productivity at day$\times$($\mu$g/mL/day)/cell number ($10^6$ cells/mL).

Four parameters were used to compare the growth and production properties of the nine cell lines:
(1) the maximum cell density during the spinner experiment
(2) the mean of the pcd values determined for samples from the early growth phase (an estimate for the productivity during the log phase)
(3) the mean of the pcd values determined for samples from the late growth phase and/or the stationary phase
(4) the maximum antibody concentration observed during the spinner experiment.

These data are summarized in Table 1.

TABLE 1

Growth and Productivity of ECB's in Spinner Flasks

| ECB | Clone | Medium | Max. viable cell density $1 \times 10^6$ cells/mL | Prod. in early growth phase (pcd) | Prod. in late growth/stationary phase (pcd) | Max. antibody conc. (mg/mL) |
|---|---|---|---|---|---|---|
| ECB1 | V354 | ProCHO4 | 0.6 | 1.8 | 2.8 | 15 |
| ECB2 | V350 | ProCHO4 | 1.3 | 7.8 | 12.4 | 113 |
| ECB3 | V349 | ProCHO4 | 1.3 | 1.7 | 3.6 | 21 |
| ECB4 | V347 | ProCHO4 | 0.9 | 5.6 | 6.2 | 63 |
| ECB5 | V348 | ProCHO4 | 0.4 | 4.5 | 5.0 | 17 |
| ECB6 | V337II | ProCHO4 | 0.7 | 5.3 | 5.4 | 34 |
| ECB7 | V337 | Excell325PF | 1.0 | 5.6 | 7.7 | 52 |
| ECB8 | V347 | Excell325PF | 1.1 | 3.2 | 5.3 | 37 |
| ECB9 | V350 | Excell325PF | 1.6 | 7.2 | 15.6 | 159 |

Two criteria regarding the production properties of the recombinant cell line, (i) a cell-specific productivity higher than 5 pcd and (ii) production of at least 50 mg/L of functional antibody were met by four ECBs, namely ECB2, ECB4, ECB7 and ECB9.

Furthermore, the recombinant antibody produced has to be as similar as possible to the hybridoma-derived anti-CD34 antibody. Therefore the antibody produced by the ECBs was compared with five different hybridoma-derived antibody lots in two different versions of the cell capture assay.

Example 5

Testing of CHO ECBs with a Dose Response Cell Capture Assay

The nine different ECBs (ECB1-ECB9) and five different lots of hybridoma-derived 9C5/9069 antibody were purified and tested in a dose response cell capture assay.

Culture supernatant was dialyzed against equilibration buffer (0.3M NaCl, 0.02M NaPO4, pH 7.4) and filtered through a 0.2-$\mu$m filter unit (Nalge Nunc). The antibodies were purified by affinity chromatography on a protein A sepharose column (Amersham Biosciences). The antibody was eluted from the column by a sodium acetate buffer (Sigma-Aldrich), pH 4.0 and dialyzed against PBS. The antibody was quantified by measuring the OD at 280 nm using 1.4 as coefficient of absorption (E 1 mg/mL).

Figure 8:
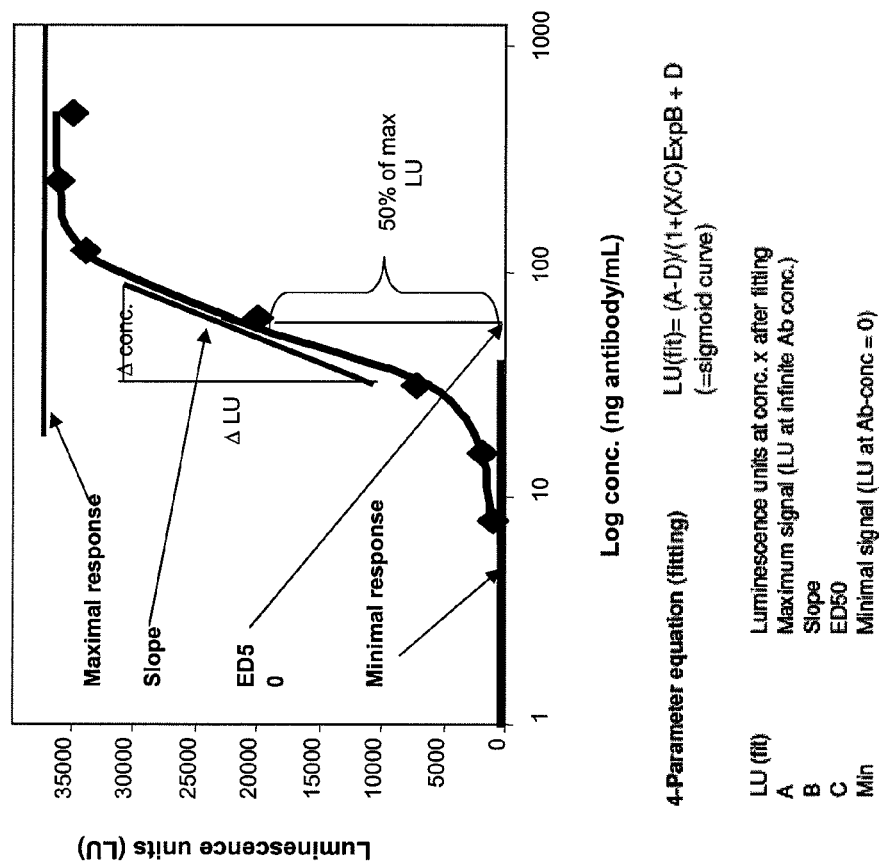
FIG. 8 shows the curve of a dose response cell capture assay using the principle of 4-parameter fit. The measured values (diamonds) of a typical experiment were fitted to the formula as shown. The resultant curve is characterized by the four parameters illustrated in the graph.

For the dose response cell capture assay 96-well microplates (Maxisorp) were coated with polyclonal antimouse IgG sheep antibody. After washing with PBS the dilution series of the respective purified recombinant hybridoma-derived anti-CD34 antibodies were analyzed. The antibodies were diluted independently three times in ProCHO4 medium supplemented with HT and glutamine (Invitrogen/Gibco) and each dilution series was tested in duplicate, resulting in six determinations. Plates were incubated overnight at 4° C. Subsequently, plates were washed with PBS. TF-1 cells were added at a cell density of $1\times10^5$ cells/mL. The Cell Titer-Glo was added after washing to remove unbound cells. The dose-dependent luminescence signals of each dilution series were fitted to the four parameter equation (FIG. 8) using the solver function of Windows Excel. FIG. 8 shows:
(i) the minimal response (corresponds to background without 9C5/9069),
(ii) the slope (reflects increase of signal in relation to increasing 9C5/9069 concentrations),
(iii) the effective dose 50% (ED50, concentration that results in 50% of the maximal response), and
(iv) the maximal response (corresponds to maximum of captured cells at saturating 9C5/9069 concentrations).

Figure 9:
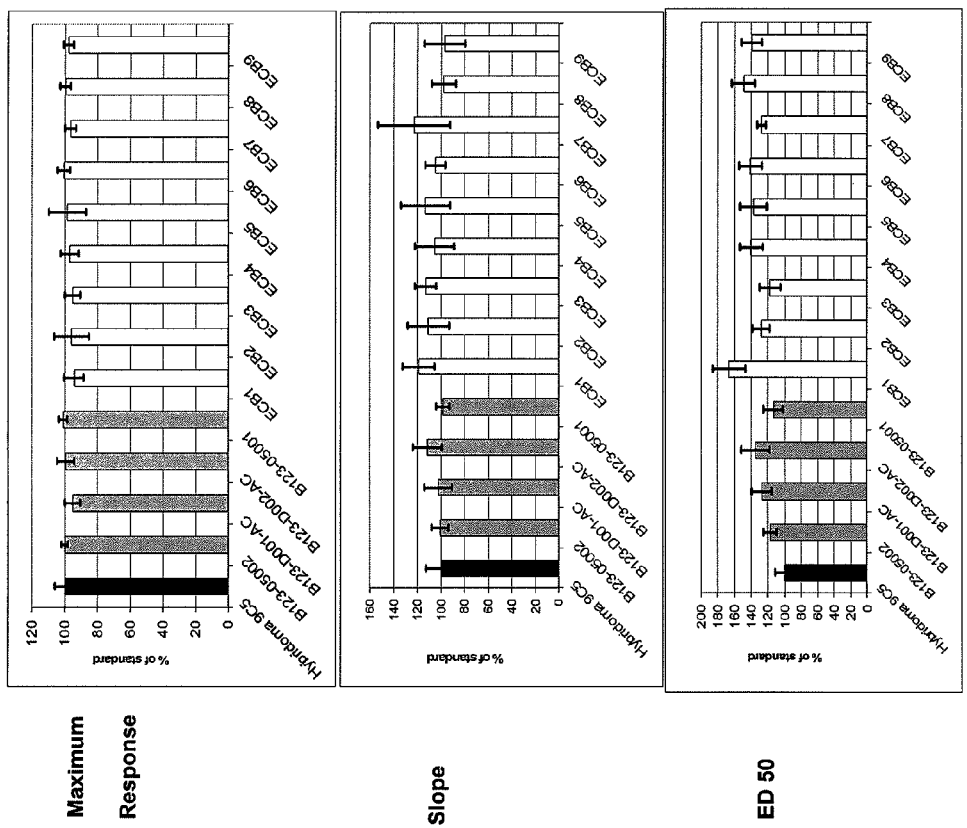
FIG. 9 shows the dose response cell capture assays of CHO cell lines expressing anti-CD34 antibody.

As the minimal response is independent from the antibody, this parameter is not considered for comparison of recombinant versus hybridoma 9C5/9069. After fitting each curve, the mean and the standard deviation of these six values were calculated for maximal response, slope and ED50. The mean obtained for the standard was set to 100% and the mean and standard deviations obtained for the recombinant or hybridoma sample tested on the same plate was expressed as a percentage of the standard. This allowed comparison of the three parameters of each of the recombinant antibody preparations (ECB-derived) with each hybridoma derived preparation, whereby the standard hybridoma preparation is equal to 100%. The results obtained for maximal response, slope and ED50 are depicted in FIG. 9. The values obtained for the hybridoma lots differed from each other. Therefore, a parameter of the recombinant anti-CD34 antibody was considered as not equivalent to hybridoma-derived antibody when the mean was not within the SD margin of at least one of the hybridoma-derived preparations. In order to select an ECB for further process development, all parameters of the respective antibody preparation have to be considered as equivalent.

Example 6

Testing of CHO ECBs with a Competition Cell Capture Assay

Purified recombinant antibodies produced by each of the ECBs were tested for their functionality in a competition assay, in which CD34 present on the surface of TF-1 cells was inhibited from binding to the antibody by increasing concentrations of release peptide PR34+.

The recombinant CHO antibodies were compared with five different lots of hybridoma-derived antibody preparations. For the competition cell capture assay 96-well microplates were coated with polyclonal sheep anti-mouse IgG antibody. After washing with PBS recombinant and hybridoma-derived anti-CD34 antibody preparations were added at a concentration of 200 ng/mL diluted in DMEM medium and supplemented with 10% fetal calf serum. Three independent dilutions of each antibody were incubated overnight at 4° C. A dilution series of the Isolex PR34+1 Stem Cell Releasing Agent was mixed with TF-1 cells to give a cell density of $1 \times 10^5$ cells/mL and peptide concentrations ranging from 50 to 800 μg/mL. Plates were washed with PBS and the TF-1/PR34+ mixtures were added. The CD34-receptor present on the surface of the TF-1 cells competes with the PR34+ for binding to the immobilized anti-CD34 antibody (Tseng-Law et al. Exp Hematol. 1999; 27:936-45). After 2 hours of incubation at 37° C. and washing to remove the unbound cells and peptide the Cell Titer-Glo was added. The dose-dependent luminescence signals of each dilution series were fitted to the four parameter equation using the solver function of Windows Excel.

Figure 10:
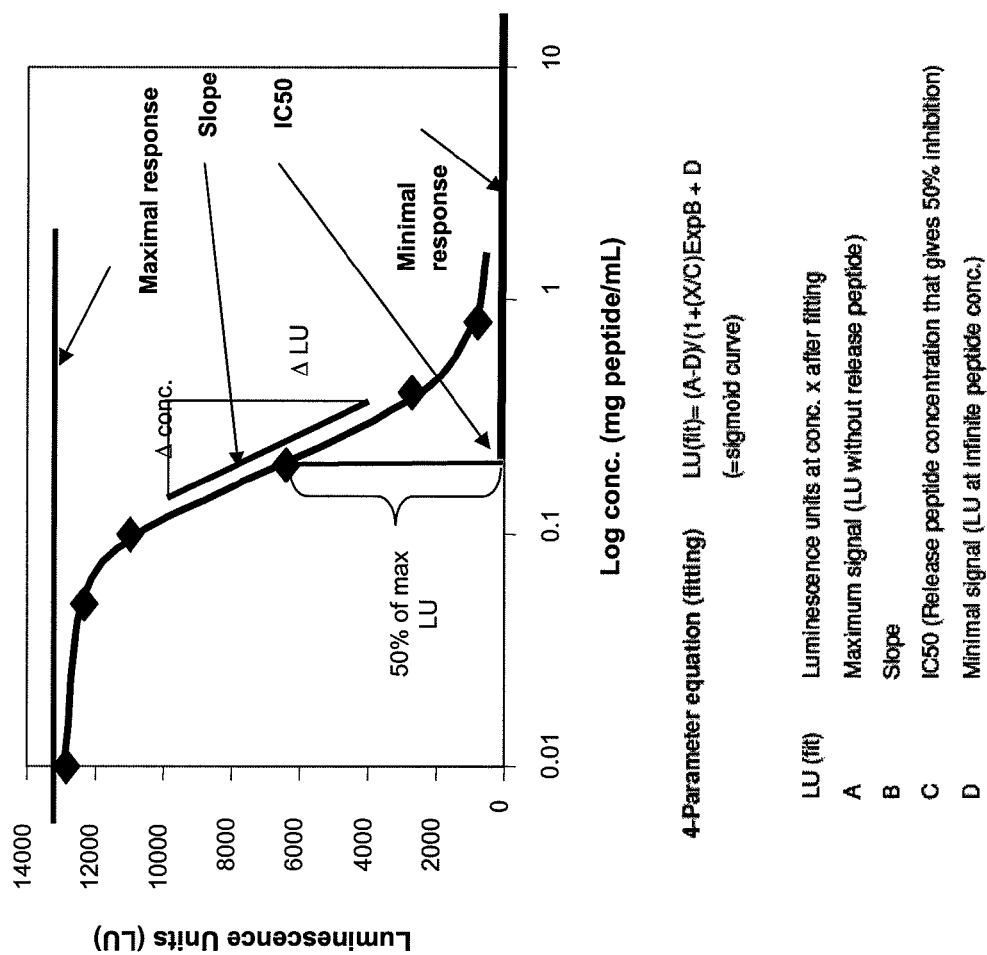
FIG. 10 shows the curve of a competition cell capture assay with release peptide using the principle of 4-parameter fit. The measured values (diamonds) of a typical experiment were fitted to the formula as shown. The resultant curve is characterized by the four parameters illustrated in the graph.

The dose-response curves obtained yielded four parameters (FIG. 10):
(i) the minimal response (corresponds to cells captured at high peptide concentrations),
(ii) the slope (reflects decrease of signal in relation to increasing PR34+ concentration),
(iii) the inhibiting concentration 50% (IC50, concentration that results in 50% of the maximal response), and
(iv) the maximal response (corresponds to maximum captured cells without PR34+).

Figure 11:
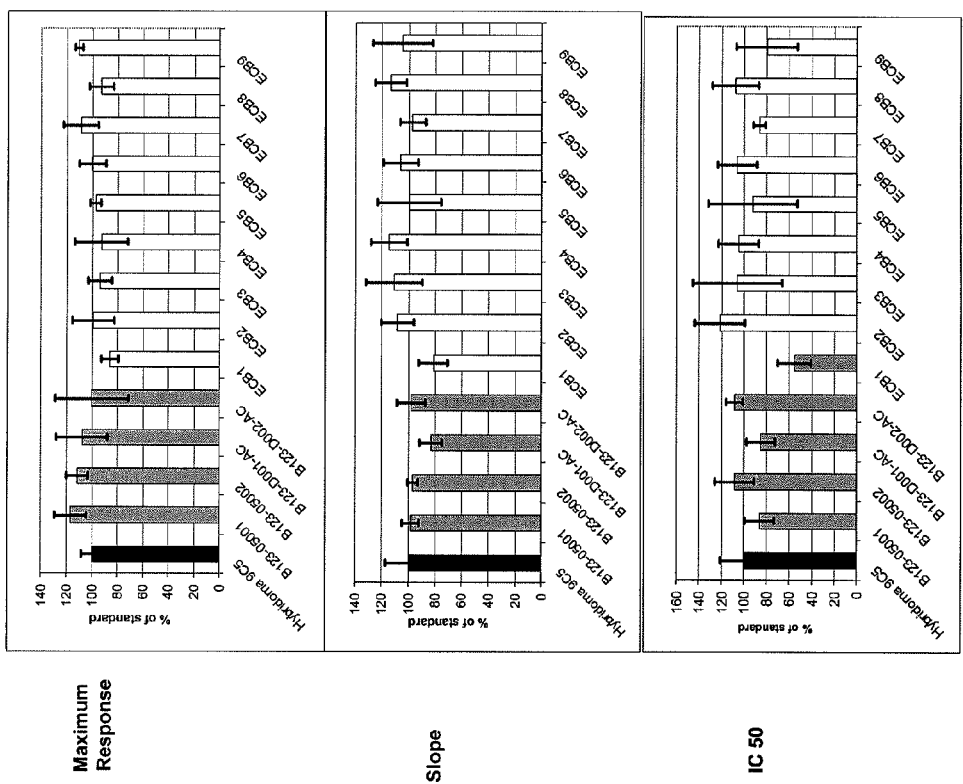
FIG. 11 shows the competition cell capture assays with release peptide of CHO cell lines expressing anti-CD34 antibody.

As the minimal response was 0 for all measurements, this parameter is not considered for comparison of recombinant versus hybridoma-derived anti-CD34 antibody. After fitting each curve, the mean and the standard deviation of the three values were calculated for maximal response, slope and IC50. The mean obtained for the standard was set to 100% and the single values for the recombinant or hybridoma samples tested on the same plate were expressed as a percentage of the standard. The means and the SDs of the obtained percentages were calculated. This allowed comparison of the three parameters of each of the recombinant anti-CD34 antibody preparations (ECB-derived) with each hybridoma derived preparation, whereby the standard-hybridoma preparation is equal to 100%. The results obtained for maximal response, slope and ED50 are depicted in FIG. 11. The values obtained for the hybridoma lots differed from each other. Therefore, a parameter of the recombinant anti-CD34 antibody was considered as not equivalent to the hybridoma-derived material when the mean was not within the SD margin of at least one of the hybridoma-derived preparations. In order to select an ECB for further process development, all parameters of the respective antibody preparation have to be considered as equivalent.

After the cell capture assays eight out of nine recombinant antibody preparations showed to be equivalent to hybridoma-derived material. ECB1 showed a striking difference: the ED50 of the dose-response curve was too high and the IC50 of the competition curve was too low, indicating that the antibody had an altered affinity to CD34. By the use of the cell capture assays ECBs which did not bind to the CD34 protein located in the membrane could be excluded and finally ECB2, ECB4, ECB7 and ECB9 met the criteria to be used in a large-scale production process for recombinant anti-CD34 antibody.

---

The invention claimed is:

1. A method for generation of a high producer cell line expressing a recombinant anti-CD34 antibody comprising the amino acid sequences set forth in SEQ ID NOS:2 and 4, wherein the method comprises the following steps:
   (a) selecting cell clones expressing high amounts of the antibody and
   (b) analyzing the expressed antibodies produced from cell clones in a cell capture assay for binding to CD34$^+$ cells, wherein the capture assay comprises
      (i) incubating the recombinant anti-CD34 antibody attached to a microplate with cells that express CD34; and
      (ii) determining the level of binding of CD34$^+$ cells to the anti-CD34 antibody.

2. The method according to claim 1, wherein the antibody is expressed in HEK293T or CHO cells.

3. The method according to claim 2, wherein the cells are adapted to protein free medium.

4. The method according to claim 2, wherein the cells are directly grown in protein free medium.

5. The method according to claim 1, wherein the cell capture assay is a dose response cell capture assay.

6. The method according to claim 1, wherein in that the cell capture assay is a competition cell capture assay.

* * * * *